US012654042B2

(12) United States Patent
Mamishev et al.

(10) Patent No.: US 12,654,042 B2
(45) Date of Patent: Jun. 16, 2026

(54) SMART INDIVIDUALIZED NEAR-FACE EXTENDED WEAR ELECTROHYDRODYNAMIC RESPIRATOR

(71) Applicant: University of Washington, Seattle, WA (US)

(72) Inventors: Alexander V. Mamishev, Seattle, WA (US); Abbie Sawyer, Seattle, WA (US); Anastasiya Makarevich, Seattle, WA (US); Richard Wang, Seattle, WA (US); Ravi Sankar Vaddi, Seattle, WA (US); Edward Martija, Seattle, WA (US); Sara Seulbee Shin, Seattle, WA (US)

(73) Assignee: University of Washington, Seattle, WA (US)

( * ) Notice: Subject to any disclaimer, the term of this patent is extended or adjusted under 35 U.S.C. 154(b) by 521 days.

(21) Appl. No.: 18/262,594

(22) PCT Filed: Jan. 26, 2022

(86) PCT No.: PCT/US2022/013844
§ 371 (c)(1),
(2) Date: Jul. 24, 2023

(87) PCT Pub. No.: WO2022/164859
PCT Pub. Date: Aug. 4, 2022

(65) Prior Publication Data
US 2024/0108923 A1        Apr. 4, 2024

Related U.S. Application Data

(60) Provisional application No. 63/142,580, filed on Jan. 28, 2021.

(51) Int. Cl.
*A62B 18/00* (2006.01)
*A61L 9/22* (2006.01)
(Continued)

(52) U.S. Cl.
CPC .............. *A62B 18/003* (2013.01); *A61L 9/22* (2013.01); *A62B 18/025* (2013.01); *A62B 18/08* (2013.01); *A62B 18/084* (2013.01); *A62B 23/02* (2013.01)

(58) Field of Classification Search
CPC ..... A62B 18/00; A62B 18/003; A62B 18/025; A62B 18/08; A62B 18/084; A62B 23/02; A61L 9/22; A61M 16/06
See application file for complete search history.

(56) References Cited

U.S. PATENT DOCUMENTS

| | | | |
|---|---|---|---|
| 2,462,005 A | 2/1949 | Schauweker |
| 5,349,492 A | 9/1994 | Kimura |

(Continued)

FOREIGN PATENT DOCUMENTS

| | | |
|---|---|---|
| CN | 105342037 A | 2/2016 |
| CN | 111065430 A | 4/2020 |

OTHER PUBLICATIONS

International Search Report for corresponding PCT application No. PCT/US2022/013844 dated May 23, 2022.

(Continued)

*Primary Examiner* — Joseph D. Boecker
(74) *Attorney, Agent, or Firm* — McDonnell Boehnen Hulbert & Berghoff LLP

(57) ABSTRACT

The present disclosure provides a device for respiratory protection. The device includes a face shield having a first end and a second end opposite the first end. The device also includes a headband coupled to the first end of the face shield and the second end of the face shield. The device also includes an electrohydrodynamic (EHD) air filter system positioned along an entirety of a perimeter of the face shield.

20 Claims, 5 Drawing Sheets

(51) Int. Cl.

| | | |
|---|---|---|
| *A62B 18/02* | (2006.01) | |
| *A62B 18/08* | (2006.01) | |
| *A62B 23/02* | (2006.01) | |

(56) References Cited

U.S. PATENT DOCUMENTS

| | | | | |
|---|---|---|---|---|
| 5,474,600 | A | * | 12/1995 | Volodina .................. B03C 3/38 |
| | | | | 96/99 |
| 5,827,407 | A | | 10/1998 | Wang |
| 5,839,432 | A | | 11/1998 | Daneshvar |
| 6,681,765 | B2 | | 1/2004 | Wen |
| 2006/0096596 | A1 | | 5/2006 | Occhialini |
| 2009/0014002 | A1 | | 1/2009 | Krafthefer |
| 2014/0205495 | A1 | * | 7/2014 | Ota ........................... A61L 9/22 |
| | | | | 422/4 |
| 2017/0361133 | A1 | | 12/2017 | Yu |
| 2021/0299319 | A1 | * | 9/2021 | Gupta ....................... A61L 2/10 |
| 2021/0386144 | A1 | * | 12/2021 | Wiklof ...................... A61L 9/22 |
| 2022/0016306 | A1 | * | 1/2022 | Prystupa ............. A61L 2103/05 |
| 2022/0080227 | A1 | * | 3/2022 | Cohen ....................... A61L 9/22 |
| 2023/0181789 | A1 | * | 6/2023 | Conrad ..................... A61L 9/22 |
| | | | | 422/121 |

OTHER PUBLICATIONS

E. D. Fylladitakis, M. P. Theodoridis, and A. X. Moronis, "Review on the history, research, and applications of electrohydrodynamics," IEEE Transactions on Plasma Science, vol. 42, pp. 358-375, 2014.

N. Brown and F. Lai, "Electrohydrodynamic gas pump in a vertical tube," in ASME 2008 Fluids Engineering Division Summer Meeting collocated with the Heat Transfer, Energy Sustainability, and 3rd Energy Nanotechnology Conferences, 2008, pp. 217-221.

Y. Liao, Z. Feng, and X. J. J. o. E. Zhou, "Predicting the pumping effects of electrohydrodynamic (EHD) gas pumps by numerical simulations and quantitative pressure drop vs. flow rate curves," vol. 96, pp. 160-168, 2018.

O. Fawole and M. Tabib-Azar, "A novel geometry for a corona wind electrohydrodynamic pump," in Sensors, 2014 IEEE, 2014, pp. 452-454.

J. Hyun, S.-G. Lee, and J. Hwang, "Application of corona discharge-generated air ions for filtration of aerosolized virus and inactivation of filtered virus," Journal of Aerosol Science, vol. 107, pp. 31-40, 2017.

M. Tański, A. Berendt, and J. Mizeraczyk, "Closed SDBD-driven two-stage electrostatic precipitator," Journal of cleaner production, vol. 226, pp. 74-84, 2019.

Y. Xiao and M. E. Torok, "Taking the right measures to control COVID-19," The Lancet Infectious Diseases, 2020.

W. Xiong, Z. Lin, W. Zhang, T. Chen, and C. Zhao, "Experimental and simulation studies on dust loading performance of a novel electrostatic precipitator with dielectric barrier electrodes," Building and Environment, vol. 144, pp. 119-128, 2018.

T.-Y. Wen, H.-C. Wang, I. Krichtafovitch, and A. V. Mamishev, "Novel electrodes of an electrostatic precipitator for air filtration," Journal of Electrostatics, vol. 73, pp. 117-124, 2015.

T.-M. Chen, C.-J. Tsai, S.-Y. Yan, and S.-N. Li, "An efficient wet electrostatic precipitator for removing nanoparticles, submicron and micron-sized particles," Separation and Purification Technology, vol. 136, pp. 27-35, 2014.

J. H. Wang, W. S. Williamson, and N. W. Sorbo, "Indoor air pollutant destruction apparatus and method using corona discharge," ed: Google Patents, 1998.

A. Zukeran, H. Sawano, K. Ito, R. Oi, I. Kobayashi, R. Wada, et al., "Investigation of inactivation process for microorganism collected in an electrostatic precipitator," Journal of Electrostatics, vol. 93, pp. 70-77, 2018.

T. A. Hamade, "Novel Application of High Voltage Electrostatics Corona Ions Discharge Related to Treatment, Sanitization and Disinfection of Biological Matter Such HIV-AIDS Infected Blood," Journal of Shanghai Jiaotong University (Science), vol. 23, pp. 112-121, 2018.

L. Zhao and K. Adamiak, "EHD flow in air produced by electric corona discharge in pin-plate configuration," Journal of Electrostatics, vol. 63, pp. 337-350, 2005.

W. Qiu, L. Xia, X. Tan, and L. Yang, "The Velocity Characteristics of a Serial-Staged EHD Gas Pump in Air," IEEE Transactions on Plasma Science, vol. 38, pp. 2848-2853, 2010.

B. Komeili, J. S. Chang, G. D. Harvel, C. Y. Ching, and D. Brocilo, "Flow characteristics of wire-rod type electrohydrodynamic gas pump under negative corona operations," Journal of Electrostatics, vol. 66, pp. 342-353, 2008/05/01/ 2008.

H. Tsubone, J. Ueno, B. Komeili, S. Minami, G. D. Harvel, K. Urashima, et al., "Flow characteristics of dc wire-non-parallel plate electrohydrodynamic gas pumps," Journal of Electrostatics, vol. 66, pp. 115-121, 2008/01/01/ 2008.

Y. T. Birhane, S. C. Lin, and F. C. Lai, "Flow characteristics of a single stage EHD gas pump in circular tube," Journal of Electrostatics, vol. 76, pp. 8-17, 2015/08/01/ 2015.

J. H. Lin, S. C. Lin, and F. C. Lai, "Performance of an electrohydrodynamic gas pump fitted within a nozzle," Journal of Electrostatics, vol. 91, pp. 1-8, 2018/02/01/ 2018.

K. Wizner, L. Stradtman, D. Novak, and R. Shaffer, "Prevalence of Respiratory Protective Devices in U.S. Health Care Facilities," Workplace Health & Safety, vol. 64, No. 8, pp. 359-368, 2016.

Tran, Anh Vang, et al. (PDF) Mechanical Structural Design of a Piezoresistive . . . Jun. 24, 2018, www.researchgate.net/publication/325980285_Mechanical_Structural_Design_of_a_Piezoresistive_Pressure_Sensor_for_Low-Pressure_Measurement_A_Computational_Analysis_by_Increases_in_the_Sensor_Sensitivity.

"Capacitive vs Piezoresistive vs Piezoelectric Pressure Sensors: The Design Engineer's Guide: Avnet Abacus." Capacitive vs Piezoresistive vs Piezoelectric Pressure Sensors | The Design Engineer's Guide | Avnet Abacus, www.avnet.com/wps/portal/abacus/solutions/technologies/sensors/pressure-sensors/core-technologies/capacitive-vs-piezoresistive-vs-piezoelectric/.

"Pressure Sensors: The Design Engineer's Guide." [Online]. Available: https://www.avnet.com/wps/portal/abacus/solutions/technologies/sensors/pressure-sensors/core-technologies/piezoelectric/. [Accessed: Sep. 15, 2020].

P. Song, Z. Ma, J. Ma, L. Yang, J. Wei, Y. Zhao, M. Zhang, F. Yang, and X. Wang, "Recent Progress of Miniature MEMS Pressure Sensors," Micromachines, vol. 11, No. 1, p. 56, 2020.

Arash, B., Jiang, J., & Rabczuk, T. (2015). A review on nanomechanical resonators and their applications in sensors and molecular transportation. Applied Physics Reviews, 2(2). doi:10.1063/1.4916728.

Poeggel, S., Tosi, D., Duraibabu, D., Leen, G., McGrath, D., & Lewis, E. (2015). Optical Fibre Pressure Sensors in Medical Applications. Sensors (Basel, Switzerland), 15(7), 17115-17148. https://doi.org/10.3390/s150717115.

\* cited by examiner

SMART INDIVIDUALIZED NEAR-FACE EXTENDED WEAR ELECTROHYDRODYNAMIC RESPIRATOR

CROSS REFERENCE TO RELATED APPLICATION

This application is a U.S. National Phase application of, and claims the benefit of, International (PCT) Application No. PCT/US2022/013844, filed Jan. 26, 2022, which claims priority to U.S. Provisional Application No. 63/142,580 filed Jan. 28, 2021, the contents of both of which are hereby incorporated by reference in their entirety.

TECHNICAL FILED

The present disclosure is in the technical field of personal protection. More particularly, the present disclosure is in the technical field of respiratory protection for personnel in healthcare, the military, and aerospace, as non-limiting examples.

BACKGROUND

Unless otherwise indicated herein, the materials described in this section are not prior art to the claims in this application and are not admitted to be prior art by inclusion in this section.

There are five categories of respirators: escape respirators, chemical/cartridge/gas mask/air-purifying respirators, self-contained breathing apparatuses (SCBAs), powered air-purifying respirators (PAPRs), and particulate respirators. Escape respirators are a one-time use escape from hazardous atmospheres, which may be immediately lethal, and are usually rated for short periods of time, around 15 minutes to one hour. The design of the escape respirator is usually either a face piece or a hood with a neck seal. Gas masks/chemical cartridges/air-purifying respirators are used in escape from hazardous atmospheres that have enough oxygen to support human life or entry into atmospheres not immediately dangerous to life.

Gas masks are also known as air-purifying respirators because of their ability to clean chemical gases or particles from the air the user will be breathing in. These masks have three categories: front-mounted or back-mounted gas masks, which denote the position of the filter; chin-style gas masks, which typically have filters attached to the face piece: and escape gas masks, which typically are only used during escape from a hazardous atmosphere. Gas masks will only work properly when the correct filter or cartridge is used. Users must know what filter to use in their situations because there is no single filter or cartridge that will purify all hazardous materials in the atmosphere. In addition to choosing the correct filter, the mask typically must be fitted for an individual as the masks need to have a clean seal around the user's nose, mouth, or face for the filter to work. When masks are not fitted for the user hazardous components in the atmosphere can enter the user's respiratory system through the unsealed areas.

SCBAs are used for entry and escape from or escape only from hazardous atmospheres. These apparatuses have two main ways to classify their air circulation systems: closed circuit, in which the user breathes in the air they breathed out previously that has undergone carbon dioxide removal and the air has been replenished of oxygen through a non-contaminated source: and open circuit, in which the user's exhalation is forced into the environment outside of the apparatus and not rebreathed, with the breathable air replenished with oxygen from a non-contaminated source. The SCBA allows the user to use the apparatus even when the atmosphere surrounding the user does not have enough oxygen to support life due to the use of an air tank. The cost of being able to survive in such a tough atmosphere is the weight of the gear, which typically totals around 30 pounds.

PAPRs use the same design for gas masks/chemical cartridges/air-purifying respirators but include a fan to make breathing easier. The same precautions must be taken as with gas masks. The user must use the correct filter for the specific hazard in the atmosphere, and in the case of a tight-fitting design, the user must be fitted for the respirator. PAPRs can be either loose or tight-fitting. The loose designs are typically fans blowing air into a hood and that air is pushed out from the bottom of the unsealed hood. This positive pressure in the hood will keep the hazardous chemicals or particulates out of the hood. Tight-fitting designs include a seal around the neck of the user. If the seal is not secure, tight-fitting PAPRs will not reliably keep the hazardous particles from contaminating the air inside the hood.

Traditional approaches to creating portable, lightweight, and quiet PAPRs have not been adequate because mechanical fans require a large volume to be housed in to reach industry standard airflow levels for PAPRs. Additionally, mechanical fans are comprised of multiple moving parts, which generate noise and have significant mass. This is a problem because the PAPRs on the market currently are large, heavy, and noisy. The bulky PAPRs are often disregarded for lighter weight, single use N95 masks or surgical masks. If PAPRs are not portable and easy to use, personnel will forego PAPRs for simpler N95 and surgical masks. Present means in the art are simply inadequate to meet and address the ease of use and portability issues.

SUMMARY

The present disclosure provides a respiratory device that incorporates electrohydrodynamic (EHD) filter technology into a perimeter of a face mask. The proposed PAPR will be lighter, quieter, smaller, and require less energy than current PAPRs on the market. These improvements upon traditional designs will make PAPRs a more viable solution for respiratory protection in the daily lives of civilians and personnel in various fields, such as the healthcare, military, and aerospace industries, as non-limiting examples. Individuals working in such situations face a heightened risk of inhaling harmful particles when tending to the ill, combating in threatening environments, or engaging with others in close proximity. The EHD device meets the size, noise, and weight requirements of end-users while still providing protection and airflow during extended use. Advantages of this approach include: a perimeter filter that prevents particle flow, a noise level that does not exceed 20 decibels, a size of unit that is less than 688 cubic centimeters, a mask that does not seal on the face so it is comfortable to wear for long durations, and a sterilization process that allows the mask to be easily sterilized after each use. The plastic shield is designed to be a half face piece where it is surrounding the nose and mouth prevents harmful particles from meeting the face or respiratory zone. The aim of the device is to have a mask that can be worn comfortably for several hours a day.

In particular, the present disclosure provides a device for respiratory protection. The device includes a face shield having a first end and a second end opposite the first end. The device also includes a headband coupled to the first end of the face shield and the second end of the face shield. The device also includes an electrohydrodynamic (EHD) air filter system positioned along an entirety of a perimeter of the face shield.

These as well as other aspects, advantages, and alternatives, will become apparent to those of ordinary skill in the art by reading the following detailed description, with reference where appropriate to the accompanying drawings.

DETAILED DESCRIPTION

Figures 1, 2:
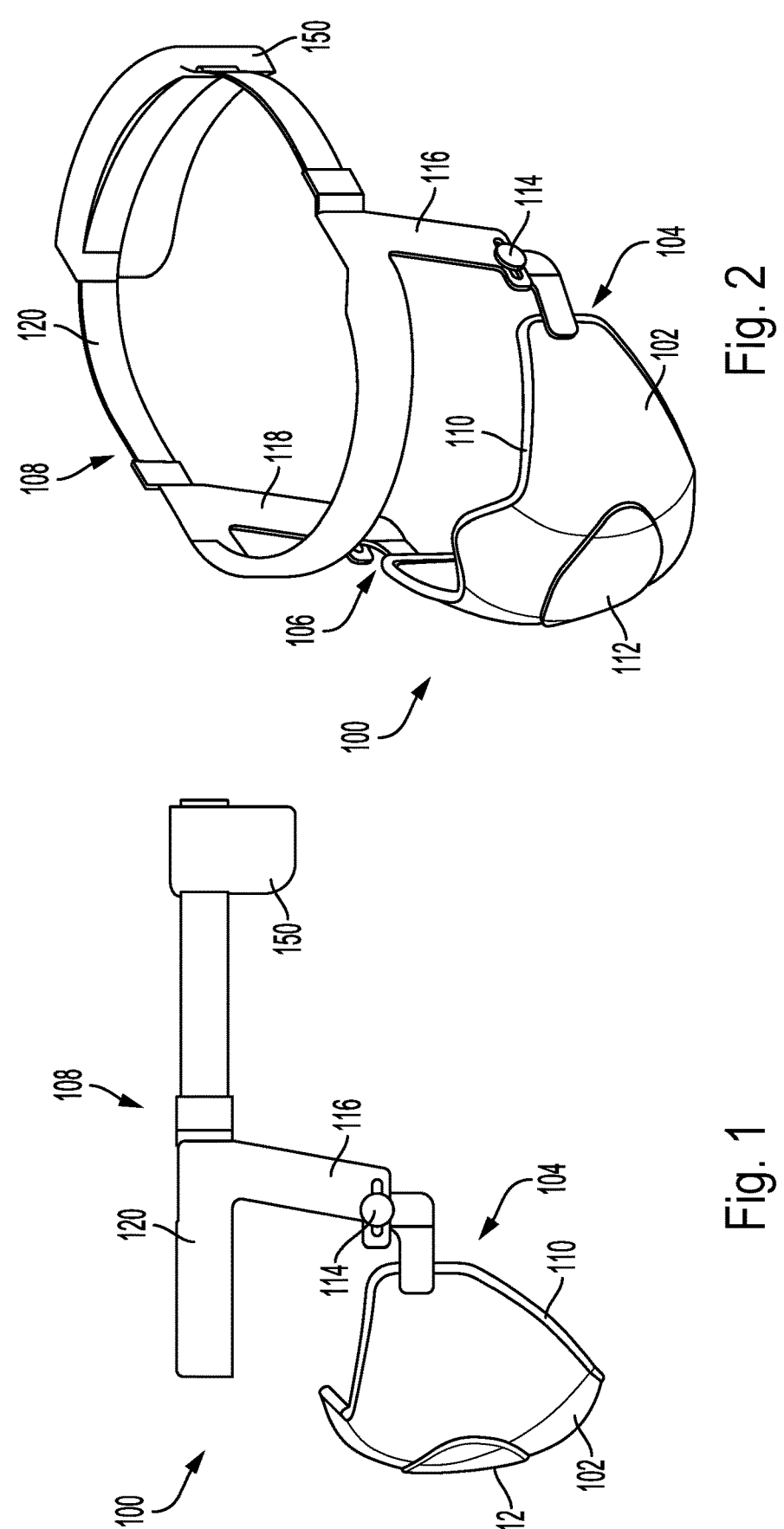
FIG. 1 illustrates an embodiment of an orthogonal left side view of an example device.
FIG. 2 illustrates an embodiment of an isometric view of the device of FIG. 1.

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the Figures, can be arranged, substituted, combined, separated, and designed in a wide variety of different configurations, all of which are explicitly contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, "coupled" means associated directly as well as indirectly. For example, a member A may be directly associated with a member B, or may be indirectly associated therewith, e.g., via another member C. It will be understood that not all relationships among the various disclosed elements are necessarily represented.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Reference herein to "one embodiment" or "one example" means that one or more feature, structure, or characteristic described in connection with the example is included in at least one implementation. The phrases "one embodiment" or "one example" in various places in the specification may or may not be referring to the same example.

As used herein, a system, apparatus, device, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

As used herein, with respect to measurements, "about" means +/−5%.

As used herein, with respect to measurements, "substantially" means +/−5%.

Generally, the present disclosure provides an electrohydrodynamic (EHD) mask that employs an EHD air filter system as a method of providing airflow.

With reference to the Figures, FIGS. 1-2 of the present disclosure provide a device 100 including a face shield 102 having a first end 104 and a second end 106 opposite the first end 104. The device 100 also includes a headband 108 coupled to the first end 104 of the face shield 102 and the second end 106 of the face shield 102. The device 100 also includes an electrohydrodynamic (EHD) air filter system 110 positioned along an entirety of a perimeter of the face shield 102.

In one example, as shown in FIGS. 1-2, the device 100 also includes a filter 112 positioned in the face shield 102 between the first end 104 and the second end 106. In one such example, the face shield 102 includes a cutout between the first end 104 and the second end 106 into which the filter 112 is positioned. In another example, the filter 112 is embedded into a material of the face shield 102. The filter 112 may comprise a federally approved filter, such as a N95 filter as a non-limiting example. Although FIGS. 1-2 illustrate a single filter 112 positioned in a central location on the face shield 102, the filter 112 may instead be offset from center. In another example, multiple filters may be positioned in the face shield 102, such as a left filter and a right filter positioned on either side of the face shield 102 (e.g., near the user's cheeks) as non-limiting examples. Such an example may facilitate viewing of the mouth of the user for improved communication while using the device 100. In another example, no filter 112 is present in the face shield 102.

The face shield 102 surrounding the nose and mouth prevents harmful particles from coming in contact with the face or respiratory zone. The face shield 102 does not contact the face of the user when in use. In one example, at least a portion of the face shield 102 comprises a transparent material. Such a transparent face shield 102 allows those who are hearing-impaired to read lips and generally provides a better indication of emotion to those interacting with the user of the device 100. The face shield 102 may be made of an anti-fog material, such as a clear plastic coated with an anti-fog polycarbonate film as a non-limiting example. The face shield 102 can be sterilized and reused, thereby providing an environmental benefit of the device 100.

In one example, the face shield 102 is adjustable to alter a distance from the face shield 102 to a face of a user. In one such example, the device 100 further includes an adjustment mechanism 114 coupled to the headband 108. The adjustment mechanism 114 enables the user to alter the distance from the face shield 102 to the face of the user. Such an arrangement enables the face shield 102 to be accurately fit to each individual face. In one example, the adjustment mechanism 114 comprises a mechanical knob that is rotated to thereby alter the distance from the face shield 102 to the face of the user.

In another example, the adjustment mechanism 114 comprises a sliding strap having a first end and a second end opposite the first end. The first end of the sliding strap is coupled to the face shield, and the second end of the sliding strap is positioned through a push button clamp. Moving the second end of the sliding strap with respect to the push button clamp alters the distance from the face shield to the face of the user. The sliding strap may be secured with a push button type clamp that allows sliding until the push button is released, and then a spring force closes the push button claim and locks the sliding strap in place. The sliding strap may include a molded end that contains a magnet for coupling and uncoupling the face shield 102 for cleaning and for changing to a different size face shield 102 as needed for a particular user. The strap may also contains electrical connections to the electronics of the device 100, as discussed in additional detail below. Other adjustment mechanisms are possible as well.

In an example, a minimum distance between the face shield 102 and the face of the user is still greater than zero such that the face shield 102 does not ever contact the face of the user. Such an embodiment helps to ensure user comfort when wearing the device 100 for long periods of time.

In one example, the face shield 102 is removably coupled to the headband 108. Such an arrangement enables face masks of varying sizes to be coupled to the headband 108 based on the particular user. In one example, the face shield 102 and/or the headband 108 includes one or more magnets that facilitate the removable connection between the face shield 102 and the headband 108. Other removable coupling mechanisms are possible as well.

As shown in FIGS. 1-2, in one example the headband 108 includes (i) a first vertical component 116 coupled to the first end 104 of the face shield 102, (ii) a second vertical component 118 coupled to the second end 106 of the face shield 102, and (iii) a circumferential component 120 coupled to the first vertical component 116 and the second vertical component 118. The circumferential component 120 is configured to contact both a front of a head of a user and a back of the head of the user when in use. In one example, a diameter of the circumferential component 120 is adjustable so that the headband 108 of the device 100 can fit users with varying sized heads, while providing comfort and repeated usage to the users.

Figure 3:
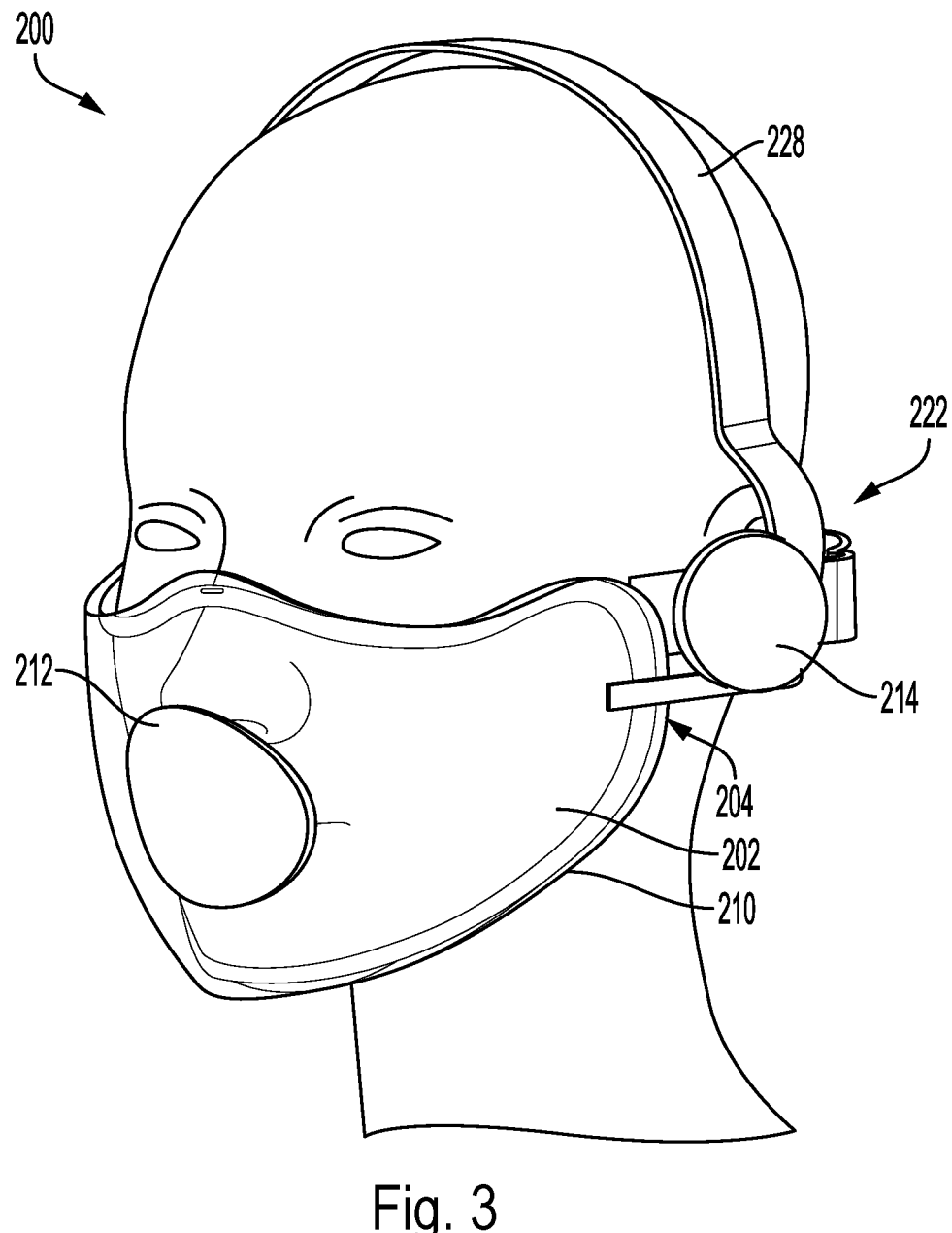
FIG. 3 illustrates an embodiment of a front view of an example device on a user.
Figure 4:
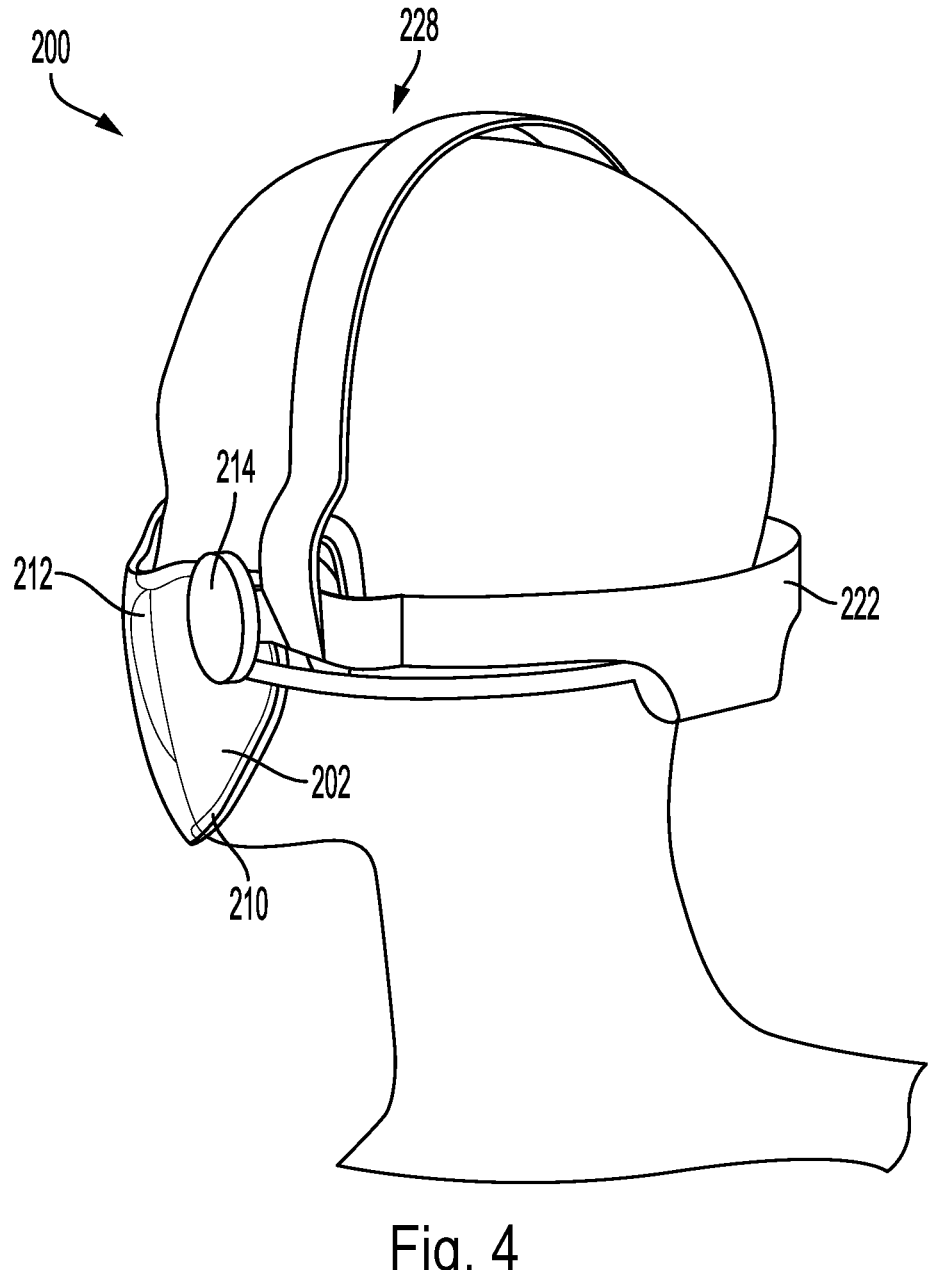
FIG. 4 illustrates an embodiment of a back view of the device of FIG. 3 on a user.

FIGS. 3-4 illustrate another example device 200 in use by a user. The device 200 may include any of the features of device 100 as described above. Further, similarly labeled components (e.g., face shield 102 and face shield 202) may be similarly configured in device 100 and device 200. As shown in FIGS. 3-4, the face shield 202 does not contact the face of the user when in use. As further shown in FIGS. 3-4, in one example the headband 208 includes a rear component 222 having a first end and a second end opposite the first end. The first end of the rear component 222 is coupled to the first end 204 of the face shield 202, the second end of the rear component 222 is coupled to the second end 206 of the face shield 202, and the rear component 222 is configured to contact a back of a head of a user when in use. In such an example, as shown in FIGS. 3-4, the headband 208 further includes a top component 228 having a first end and a second end opposite the first end. The face shield 202 is held on the head of the user by the top component 228 above the head, with the weight distributed equally on both sides of the top component 228. The first end of the top component 228 is coupled to the rear component 222 adjacent the first end of the rear component 222, the second end of the top component 228 is coupled to the rear component 222 adjacent the second end of the rear component, and the top component 228 is configured to contact a top of the head of the user when in use. In one example, a length of one or more of the rear component 222 and the top component 228 are adjustable so that the headband 208 of the device 200 can fit users with varying sized heads, while providing comfort and repeated usage to the users.

In another example, the first end of the top component 228 is coupled directly to the first end 204 of the face shield 202, the first end of the rear component 222 is coupled to the top component 228 adjacent the first end of the top component 228, the second end of the top component 228 is coupled directly to the second end 206 of the face shield 202, and the second end of the rear component 222 is coupled to the top component 228 adjacent the second end of the top component 228.

In yet another example, the headband 208 does not include the rear component 222 and instead only includes the top component 228. In such an example, the first end of the top component 228 is coupled directly to the first end 204 of the face shield 202, the second end of the top component 228 is coupled directly to the second end 206 of the face shield 202.

Figure 5:
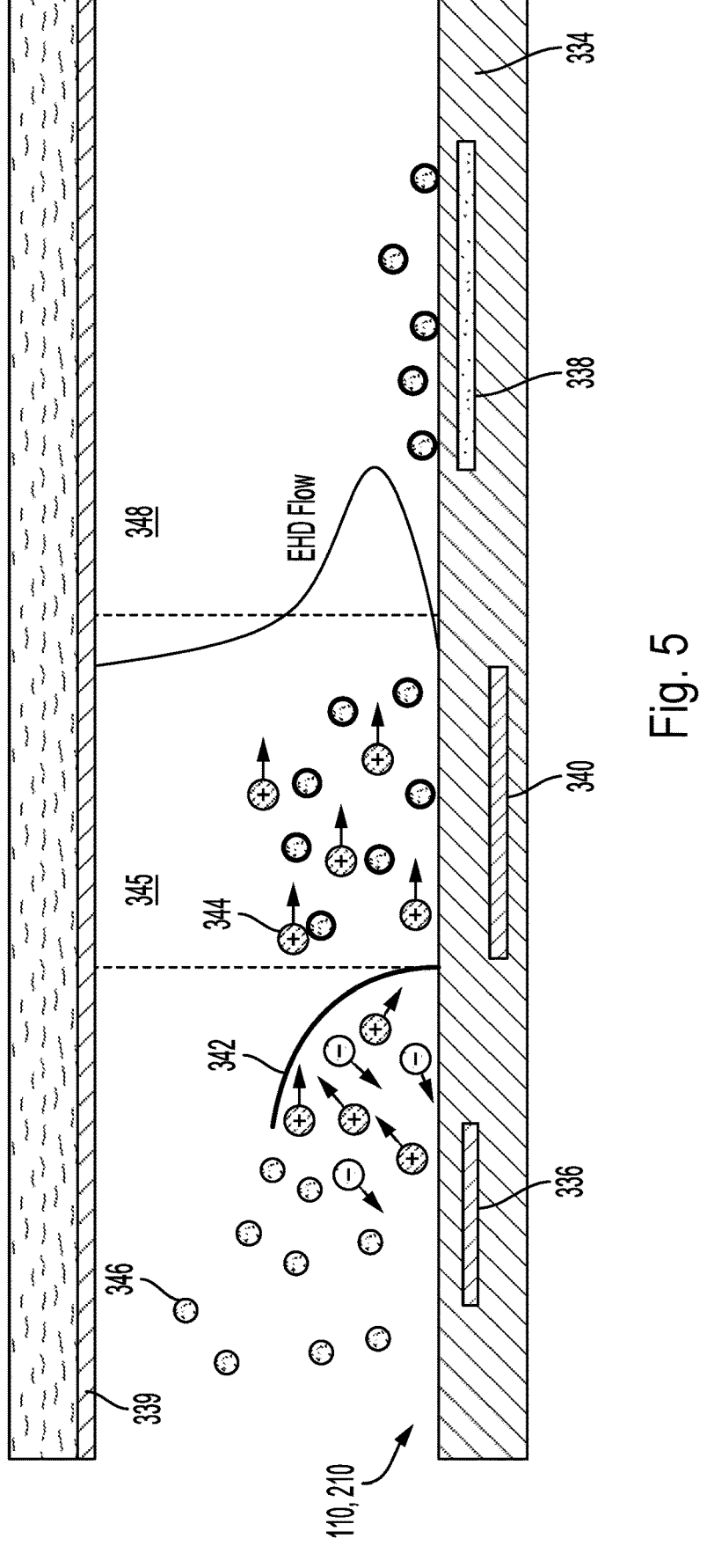
FIG. 5 illustrates an embodiment of the electrohydrodynamic (EHD) air filter system.

The principle of operation of the EHD air filter system 110, 210 is depicted in FIG. 5. As shown in FIG. 5, the EHD air filter system 110, 210 can include a dielectric layer 334, an emitter 336 positioned in the dielectric layer 334, a collection electrode 338 positioned in the dielectric layer 334, and a ground electrode 340 positioned in the dielectric layer 134 between the emitter 336 and the collection electrode 338. The EHD air filter system 110, 210 is shown spaced away from the skin 339 of a user. In use, when a high voltage is applied between the collection electrode 338 and the ground electrode 340 separated by the dielectric layer 334, the neutral particles 346 (such as air molecules as a non-limiting example) are ionized by the strong electric field induced by the emitter 336 on the surface of the dielectric layer 334 in an ionization region 342. The high velocity ions 344 collide with the neutral particles 346 driving the EHD flow. Particles 346 aspirated by the EHD flow travel through the ionization region 342 where the high velocity ions 344 bombard the particles 346, thereby imparting a charge in the charging region 345. The Coulomb force caused by the electric field between the emitter 336 and the collection electrode 138 forces the particles 146 towards the collection electrode 338. As shown in FIG. 5, the EHD air filter system 110, 210 aspirates the particles 346 into the dielectric barrier discharge induced flow, rapidly charges the particles 346 in the charging region, and collects the charged particles 346 on the collection electrode 338 in a collection region 348. High ion concentration and the strong electric field between the emitter 336 and the collection electrode 338 result in high collection efficiencies.

The EHD air filter system 110, 210 described herein has no moving parts. Instead, the pumping action of the EHD air filter system 110, 210 pump is driven by the large potential difference between the emitter 336 and collection electrode 338. This allows for lower maintenance requirements as static parts do not wear as quickly compared to moving parts. Additionally, a static air filter system decreases the amount of noise generated and contains fewer components, effectively decreasing the weight of the air filter system. Furthermore, the static design allows for a more efficient pumping of air as there is no energy loss in the friction between moving parts.

By integrating the EHD air filter system 110, 210 into the face shield 10, 202, the proposed solution will not burden the user with the task of attaching a hose and unit onto their body. The user will not need to burden themselves with heavy machinery and will no longer be wary of catching their extended breathing tubes on the surrounding environment. The device 100 described herein is designed to surpass other PAPRs in size, weight, and ease of use. The advantages of the present device 100, 200 include, without limitation, a PAPR that is both lightweight, small, and quiet unlike any other PAPR. These characteristics make the device 100, 200 described herein a more practical option traditional PAPR devices. The EHD air filter system 110, 210 is small enough to fit into the perimeter of the face shield 102, 202, as discussed above. Both the lightweight and position of the EHD air filter system 110, 210 make the device 100, 200 easy to use, as the user does not need to worry about external parts. The user will be able to fully focus on their task at hand without being distracted by the constant sound of a fan or other moving parts. Additionally, communication will be improved for the user since there is no longer a need to shout over the sound of a fan, and other users will not need to strain their ears to hear someone speaking.

As discussed above, the EHD air filter system 110, 210 is positioned along an entirety of the perimeter of the face shield 102, 202. Due to the compound and reverse curves on the perimeter of the face shield 102, 202, installing wire or ribbon cable electrodes on that periphery may be difficult, especially with a high degree of tolerance. Therefore, in one example, each of the emitter 336, the collection electrode 338, and the ground electrode 340 are vacuum deposited along the entirety of the perimeter of the face shield 102, 202. In another example, the EHD air filter system 110, 210 includes one or more dielectric layers, a plurality of emitters positioned in the one or more dielectric layers, a plurality of collection electrodes positioned in the one or more dielectric layers, and a plurality of ground electrodes positioned in the one or more dielectric layers between the plurality of emitters and the plurality of collection electrodes. As such, a plurality of segments of the emitter 336, the collection electrode 338, and the ground electrode 340 can be fastened to the perimeter of the face shield 102, 202 without excessive bending.

Figure 6:
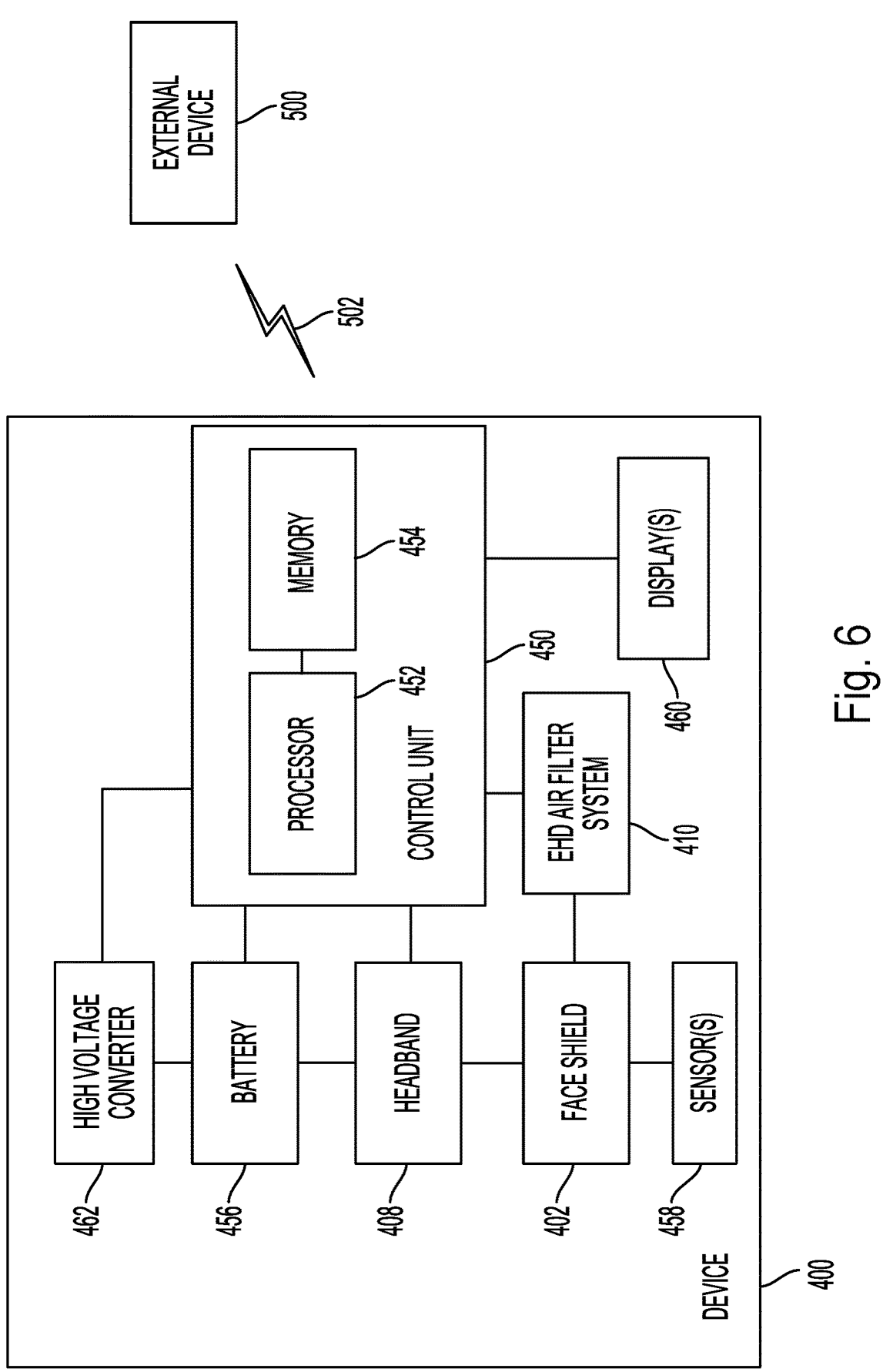
FIG. 6 illustrates a simplified block diagram containing an overview of the components of a device.

FIG. 6 illustrates a simplified block diagram containing an overview of the components of a device 400. The device 400 may include any of the features described above with respect to devices 100, 200. Further, similarly labeled components (e.g., face shield 102, face shield 202, and face shield 402) may be similarly configured in each of devices 100, 200, and 400. As shown in FIG. 6, the device 400 may further include a control unit 450 positioned on the headband 408. The control unit 450 is configured to regulate airflow from the EHD air filter system 110. The control unit 450 may be connected to the face shield 402 via wirings. The control unit 450 can be any type of controller including, but not limited to, a microprocessor, a microcontroller, a digital signal processor, or any combination thereof. The control unit 450 includes a processor 452 and on-board data storage, such as memory 454 coupled to the processor 452. The memory 454 may store software that can be accessed and executed by the processor 452, for example. The memory 454 can include any type of memory now known or later developed including but not limited to volatile memory (such as RAM), non-volatile memory (such as ROM, flash memory, etc.) or any combination thereof. The control unit 450 may include program instructions that are stored in the memory 454 (and/or possibly in another data-storage medium) and executable by the processor 452 to facilitate the various functions described herein. Although various components of the device 400 are shown as distributed components, it should be understood that any of such components may be physically integrated and/or distributed according to the desired configuration of the device 400.

As shown in FIG. 6, the device 400 also includes a battery 456 positioned on the headband 408. In one example, the battery 456 may be stored in a rear battery compartment coupled to the headband 4080. In another example, the battery 456 may be formed to fit within the headband 108. In one example, the battery 456 may be rechargeable and may be configured to power the device 400 for a minimum of eight hours. In one example, the device 400 may include a battery hatch that will hold the battery 456. A charging port may be positioned on this hatch as well for more user convenience. The battery hatch and charging port may be connected by a charging circuit. In such an example, the battery 456 can either be removed and charged or kept in the hatch and charged.

As shown in FIG. 6, the device 400 may also include one or more sensors 458 positioned on the face shield 402. In one example, the one or more sensors 458 comprise proximity sensors. Other sensors are possible as well. In one example, the control unit 450 is configured to (i) detect, via the one or more sensors 158, a distance between the face shield 402 and a face of a user, and (ii) activate the EHD air filter system 410 if the detected distance is within a threshold distance. In one example, the threshold distance comprises an acceptable range of distances between the face shield 402 and a face of the user in which the EHD air filter system 410 can properly operate. The EHD air filter system 410 may be similarly configured to the EHD air filter systems 110, 210 described above in relation to FIGS. 1-5.

In one example, the device 400 may further include one or more displays 460 in communication with the control unit 450. The one or more displays 460 may be positioned on the face shield 402, as a non-limiting example. In use, the one or more displays 460 may provide an indication of an operating state of the device 400. For example, the one or more displays 460 may provide a first visual indication if the EHD air filter system 410 is active (e.g., one or more green LEDs), and the one or more displays 460 may provide a second visual indication if the EHD air filter system 410 is not active (e.g., one or more red LEDs). Other colors and examples of displays are possible as well. Additionally or alternatively, the device 400 may include one or more speakers configured to provide an audible indication of an operating state of the device 400.

As shown in FIG. 6, the device 400 may further include a high voltage converter 462. Since the EHD air filter system 410 will need to operate with voltages ranging from 3 kV to 15 kV, a HV DC to AC converter that is both lightweight and small may be integrated into the device 400.

In another example, the control unit 450 is configured to (i) in response to detecting that the face shield 402 is coupled to the headband 408, activate the one or more sensors 458. As described above, in one example the face shield 402 and/or the headband 408 includes one or more magnets that facilitate the removable connection between the face shield 402 and the headband 408. In such an example, the magnetic connection may trigger the control unit 450 to activate the one or more sensors 458 to detect the distance between the face shield 402 and a face of a user. In one example, the magnetic connection between the face shield 402 and the headband 408 completes an electrical circuit that automatically triggers the control unit 450 to activate the one or more sensors 458.

In another example, the control unit 450 is configured to (i) detect, via the one or more sensors 458, a sneeze or a cough of a user, and (ii) deactivate the EHD air filter system 410 for a time period after the detected sneeze or cough. The time period may range from 2 to 10 seconds, as a non-limiting example. Further, after the time period has elapsed the control unit 450 may cause the EHD air filter system 410 to be activated with a higher exhalation flow for a period of time to remove water vapor that may be present on the interior of the face shield 402 after the sneeze or cough.

In one example, the one or more sensors 458 comprise one or more accelerometers, and the sneeze or cough of the user may be detected by detecting a spike in acceleration over a short time period, such as 1 second. In another example, the one or more sensors 458 comprise one or more microphones, and the sneeze or cough of the user may be detected by detecting a spike in audio data (e.g., a detected decibel level) over a short time period, such as 1 second. In another example, the sneeze or cough of the user may be detected by detecting closed eyes of the user via the one or more sensors 458. In such an example, the one or more sensors may include one or more inward-facing proximity sensors directed towards the eye, one or more inward-facing cameras directed towards the eye, one or more inward-facing light sources (e.g., infrared LEDs) directed towards the eye and one or more corresponding detectors, among other possible sensor configurations. The control unit 450 may determine that the sensor data is indicative of a sneeze or cough by a combination of the above-described methods. Other examples are possible as well.

In another example, the control unit 450 is configured to (i) detect, via the one or more sensors 458, a count of a number of sneezes or coughs of the user, and (ii) transmit a message to an external device 500 if the count exceeds a threshold. By collectively monitoring and comparing incidences of coughing and sneezing, the one or more sensors 458, coupled to the Internet of things capability, may be configured to generate data regarding possible health issues within a facility. This data can be used to find emerging health problems in groups or individuals within the facility.

In one example, the device 400 communicates with an external device 500 using a communication link 502, such as a wired or wireless connection. The external device 500 may be any type of device that can receive data and display information corresponding to or associated with the data. For example, the external device 500 may be a mobile phone, a tablet, or a personal computer as examples. The device 400 and the external device 500 may contain hardware to enable the communication link 502, such as processors, transmitters, receivers, antennas, etc.

In FIG. 6, the communication link 502 is illustrated as a wireless connection; however, wired connections may also be used. For example, the communication link 502 may be a wired link via a serial bus such as a universal serial bus or a parallel bus. A wired connection may be a proprietary connection as well. The communication link 502 may also be a wireless connection using, e.g., Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Since many modifications, variations, and changes in detail can be made to the described example, it is intended that all matters in the preceding description and shown in the accompanying figures be interpreted as illustrative and not in a limiting sense. Further, it is intended to be understood that the following clauses (and any combination of the clauses) further describe aspects of the present description.

We claim:

1. A device comprising:
a face shield having a first end and a second end opposite the first end;
a headband coupled to the first end of the face shield and the second end of the face shield; and
an electrohydrodynamic (EHD) air filter system positioned along an entirety of a perimeter of the face shield.

2. The device of claim 1, further comprising:
a filter positioned in the face shield between the first end and the second end.

3. The device of claim 2, wherein the face shield includes a cutout between the first end and the second end into which the filter is positioned.

4. The device of claim 2, wherein the filter is embedded into a material of the face shield.

5. The device of claim 1, wherein the face shield is adjustable to alter a distance from the face shield to a face of a user.

6. The device of claim 5, further comprising an adjustment mechanism coupled to the headband, wherein the adjustment mechanism enables the user to alter the distance from the face shield to the face of the user.

7. The device of claim 6, wherein the adjustment mechanism comprises a mechanical knob that is rotated to thereby alter the distance from the face shield to the face of the user.

8. The device of claim 6, wherein the adjustment mechanism comprises a sliding strap having a first end and a second end opposite the first end, wherein the first end of the sliding strap is coupled to the face shield, wherein the second end of the sliding strap is positioned through a push button clamp, and wherein moving the second end of the sliding strap with respect to the push button clamp alters the distance from the face shield to the face of the user.

9. The device of claim 1, wherein the face shield is removably coupled to the headband.

10. The device of claim 1, wherein the face shield does not contact the face of the user when in use.

11. The device of claim 1, wherein the headband comprises:
   a first vertical component coupled to the first end of the face shield;
   a second vertical component coupled to the second end of the face shield; and
   a circumferential component coupled to the first vertical component and the second vertical component, wherein the circumferential component is configured to contact both a front of a head of a user and a back of the head of the user when in use.

12. The device of claim 1, wherein the headband comprises:
   a rear component having a first end and a second end opposite the first end, wherein the first end of the rear component is coupled to the first end of the face shield, wherein the second end of the rear component is coupled to the second end of the face shield, and wherein the rear component is configured to contact a back of a head of a user when in use; and
   a top component having a first end and a second end opposite the first end, wherein the first end of the top component is coupled to the rear component adjacent the first end of the rear component, wherein the second end of the top component is coupled to the rear component adjacent the second end of the rear component, and wherein the top component is configured to contact a top of the head of the user when in use.

13. The device of claim 1, wherein the EHD air filter system comprises:
   a dielectric layer;
   an emitter positioned in the dielectric layer;
   a collection electrode positioned in the dielectric layer; and a ground electrode positioned in the dielectric layer between the emitter and the collection electrode.

14. The device of claim 13, wherein each of the emitter, the collection electrode, and the ground electrode are vacuum deposited along the entirety of the perimeter of the face shield.

15. The device of claim 1, wherein the EHD air filter system comprises:
   one or more dielectric layers;
   a plurality of emitters positioned in the one or more dielectric layers;
   a plurality of collection electrodes positioned in the one or more dielectric layers; and
   a plurality of ground electrodes positioned in the one or more dielectric layers between the plurality of emitters and the plurality of collection electrodes.

16. The device of claim 1, further comprising:
   a control unit positioned on the headband, wherein the control unit is configured to regulate airflow from the EHD air filter system;
   a battery positioned on the headband; and
   one or more sensors positioned on the face shield.

17. The device of claim 16, wherein the control unit is configured to:
   detect, via the one or more sensors, a distance between the face shield and a face of a user; and
   activate the EHD air filter system if the detected distance is within a threshold distance.

18. The device of claim 1, wherein the control unit is configured to:
   in response to detecting that the face shield is coupled to the headband, activate the one or more sensors.

19. The device of claim 1, wherein the control unit is configured to:
   detect, via the one or more sensors, a sneeze or a cough of a user; and
   deactivate the EHD air filter system for a time period after the detected sneeze or cough.

20. The device of claim 19, wherein the control unit is configured to:
   detect, via the one or more sensors, a count of a number of sneezes or coughs of the user; and
   transmit a message to an external device if the count exceeds a threshold.

* * * * *